June 5, 1973 S. McGREDY IV Plant Pat. 3,351
ROSE PLANT
Filed March 3, 1971
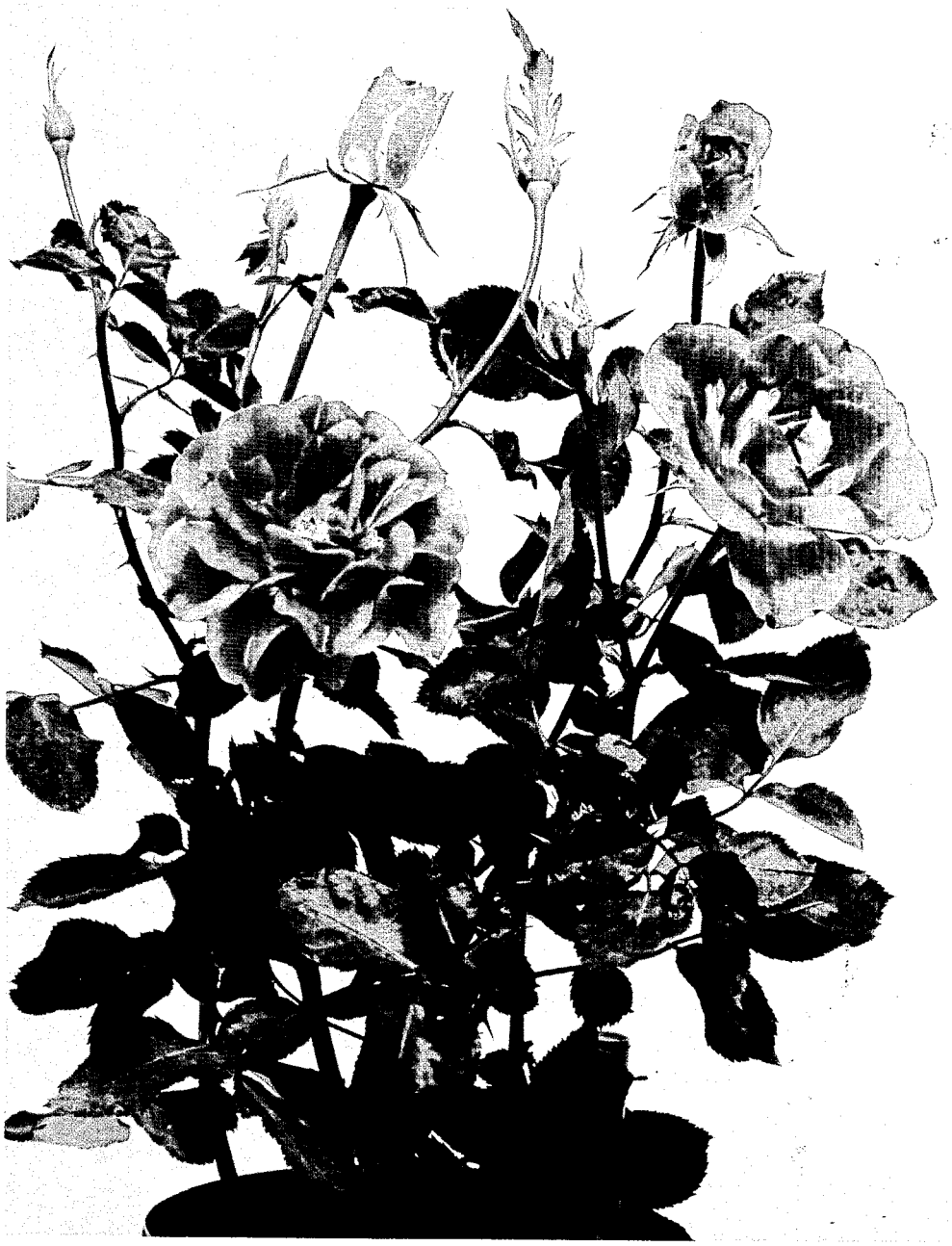

United States Patent Office

Plant Pat. 3,351
Patented June 5, 1973

3,351
ROSE PLANT

Samuel McGredy IV, Portadown, Northern Ireland, assignor to Armstrong Nurseries, Inc., Ontario, Calif.

Filed Mar. 3, 1971, Ser. No. 120,782
Claims priority, application Great Britain, Mar. 9, 1970, AFB/5/138
Int. Cl. A01h 5/00
U.S. Cl. Plt.—20 1 Claim

ABSTRACT OF THE DISCLOSURE

A hardy spreading bush rose of the floribunda class characterized primarily by striking color difference between margins and centers of the flower petals, the margins being distinctly pale, particularly where the plants are grown in areas of low light intensity, the plant being of the spreading type, thickly branched, displaying new leaves with an inconspicuous raised dark green area, the peduncles, although otherwise smooth, having a number of very small short stipitate glands.

This invention relates to a new rose plant of the floribunda class. The plant is a seedling of the hardy, spreading bush type, cultivated primarily for garden decoration.

Although the new variety was originally propagated in Portadown, County Armagh, Northern Ireland, the description which here follows was made from a plant budded and grown in Ontario, Calif., from the Irish stock.

The seed parent of this new variety was "Marlena," the pollen parent being an unnamed seedling which was derived by crossing "Evelyn Fison"×("Orange Sweetheart"×"Fruhlingsmorgen"). The plant holds its distinguishing characteristics through succeeding propagations by budding.

This new variety usually bears its flowers singly, on normal strength, short stems. Sometimes, however, the flowers are borne in irregular rounded clusters of three to five, or more, to a stem. The plant blooms freely outdoors, and nearly continuously during the growing season. The bloom has a slight fragrance.

The differences between this new variety of rose plant and its seed parent, Marlena, include the following features:

The flowers of Marlena would normally be described as dark red, but the new cultivar displays a variety of shades of red and is particularly distinguished by the variation in color between the inner portion of the bloom and the outer petals. Furthermore, the margins of the petals of the new variety contrast with the color of the center, particularly if grown in areas of low light density, such as Northern Ireland.

The plants of Marlena are low growing and somewhat spreading, but they are not as vigorous, as spreading, or as thickly branched as plants of the new cultivar. Most of the flowers of the new cultivar are borne on single stems, whereas the seed parent bears a larger proportion of its blooms in clusters.

The juvenile leaves of this new cultivar have inconspicuous but nevertheless discernible dark green raised spots, which are not found in the foliage of Marlena at any stage of its growth. This new cultivar has many more large prickles and somewhat more small prickles than its seed parent, and these prickles are smaller and more slender in their proportions, both as to base and length, than Marlena's prickles.

The stems of this new variety are shorter and stiffer than the characteristic stems of the Marlena cultivar.

The differences between this new cultivar and its pollen parent, Evelyn Fison×(Orange Sweetheart×Fruhlingsmorgen), include the matters stated below:

The flowers of this new cultivar are semi-double and their color system is quite unique. The cultivar Evelyn Fison has scarlet flowers which are double in petalage, whereas the new cultivar petalage is only semi-double. In the new cultivar, the cluster of flowers is usually small, whereas the clusters of Evelyn Fison are broad. Indeed, the entire plant of this new cultivar is substantially larger than the plants of the Evelyn Fison rose, and much more thickly branched.

The color of the flowers of this new variety, and the petalage of it, are quite different from Orange Sweetheart. Further, this new cultivar is a much more vigorous plant, more densely branched and more spreading in habit than is the cultivar Orange Sweetheart.

As compared to the remaining member of the group, the cultivar Fruhlingsmorgen is classified as a shrub rose, whereas the new variety is a floribunda. The habit of these plants is strongly different. The new cultivar is thickly branched and dense, with abundant foliage covering, while the plants of Fruhlingsmorgen are rangy and tall in habit and tend to be rather sparsely provided with foliage. Also, this new cultivar has flowers which are semi-double in petalage, whereas Fruhlingsmorgen has flowers which are characteristically single, and have five petals. Further, this new cultivar seldom sets hips, and when it does they do not persist. The cultivar Fruhlingsmorgen, on the other hand, sets hips freely, which persist and are very colorful.

The accompanying drawing illustrates the plant in color and shows the flowering thereof from bud to full bloom.

Throughout this specification, color names beginning with a small letter signify that the name of that color, as used in common speech, is aptly descriptive. Color names beginning with a capital letter designate values based upon the Nickerson Color Fan, put out by Munsell Color Co.

*Bud*

The peduncle is short, slender to average caliper, erect, and usually smooth, but with several to many small stipitate glands. Its color is near Light Olive, 10Y 5/5, overlaid with near Moderate Yellowish Brown, 10YR 4/4, on the side exposed to the sun.

Before the calyx breaks, the bud is small, short and ovoid in form.

As the calyx breaks, the color is near Dark Red, 2.5R 3/7. The inner surface of the sepals carries a fine, woolly tomentum.

The margins of alternate sepals are lined with a fine, woolly tomentum; margins of others are lined with many small stipitate glands and small slender foliaceous parts. The outside surface of the sepals is usually smooth, with from none to few small stipitate glands. Usually, the foliaceous parts extend to one-third of the sepal length.

As the first petal opens, the bud is small, short, and ovoid in form. The color on the outside of the petal is near Strong Red, 5R 4/12. The inside surface of the petal is between Vivid Red, 5R 5/13, and Strong Red, 2.5R 5/12. The bud opens up well, and is not retarded or prevented from opening by cold, hot, wet, or dry weather.

*Bloom*

The size of the bloom when fully open is small, being from 2½ inches to 3⅓ inches across. The petalage is semi-double, with from 15 to 25 petals, plus from 5 to 8 petaloids arranged irregularly. The bloom is cupped at first, becoming flat.

At first the petals are loosely cupped, becoming later at maturity loosely flat. They are of medium thickness, moderately leathery, with inside slightly velvety and outside satiny. The outside petals are between round and broadly obovate, with apex flat. The intermediate petals are broadly obovate, with apex rounded. The inside petals are obovate, also with apex rounded. The colors may be modified by being shaded and/or washed with other colors.

The paragraphs immediately following describe color values observed in a flower newly opened in the month of October. The plant had been grown outdoors in Ontario, Calif.

The outer surface of the outside petal is near Moderate Red, 2.5R 4/10. The inner surface of the outside petal is between Moderate Red, 2.5 4/10, and Strong Red, 5R 4/12.

The intermediate and inner petals are the same in coloration, being near Strong Purplish Pink, 7.5RP 7/10, on the outer surface and between Moderate Red, 2.5R 4/10, and Strong Red, 5R 4/12, on the inner surface.

The paragraphs immediately following describe the color values observed in a bloom which had been open for three days, outdoors, in the month of October. The plant had been grown outdoors in Ontario, Calif.

The outer surface of the outside petal was between Strong Purplish Red, 10RP 4/12, and Strong Purplish Red, 7.5RP 4/11. The inner surface of the outside petal was near Strong Purplish Red, 10RP 4/12, with approximately one-fifth of the petal width in the area along the edges and apex of the petal being near Deep Purplish Pink, 7.5RP 6/12.

The outer surface of the inside petal was near Light Purplish Pink, 5RP 8/5. The inner surface of the inside petal was between Strong Red, 5R 4/12, and Moderate Red, 2.5R 4/10, with approximately one-fifth of the petal width in the area along the edges and apex of the petal being near Deep Purplish Pink, 7.5RP 6/12.

The general color effect of the newly opened flower is between Moderate Red, 2.5R 4/10, and Strong, Red, 5R 4/12. The bloom after being three days open gives a general color effect of from Moderate Red, 2.5R 4/10 to Strong Purplish Red, 10R 4/12. The petals drop off cleanly, and are not particularly affected in this respect by cold, hot, wet, or dry weather.

The flower on the bush in the garden persists for from three to five days in the month of November, in Ontario, Calif. Cut flowers grown outdoors and kept at living-room temperatures persisted for two to three days in the month of November.

*Reproductive organs*

Stamens: The stamens are average in numbers, and are arranged regularly about the pistils.

Filaments: The filaments are short to medium length, being 4 to 10 mm. in length, and near Brilliant Greenish Yellow, 7.5Y 9/8, in color. Most are with anthers.

Anthers: The anthers are small to medium in size, all opening approximately at once. On both the upper and lower sides the margins are near Moderate Orange Yellow, 10YR 8/10, the remainder being near Brilliant Yellow, 5Y 9/9.

Pollen: The pollen is sparse, and near Strong Orange Yellow, 10YR 7/10, in color.

Pistils: The pistils are few to average in number, approximately 40.

Styles: The styles are uneven, short, thin caliper, and bunched, being near Brilliant Yellow Green, 2.5GY 9/8, in color.

Stigma: The stigma is near Brilliant Greenish Yellow, 10Y 9/9.

Ovaries: The ovaries are usually all enclosed in the calyx.

Hips: Hips are somewhat rare, and are found only at the end of the season on young plants. They are small, short, and globular in form and smooth.

Sepals: The sepals are persistent, but not permanent. They are short to medium-length, straight to spear-shaped, and curled to recurved. The color is not significant.

Seeds: Seeds are few, being 5 to 10 in number, and are small in size.

*Foliage*

The compound leaves usually comprise three to seven leaflets. They are abundant, small to medium in size, leathery, and semi-glossy in texture. The leaflets are oval, with apex acute, base round, and margin simply serrate. Small inconspicuous dark green raised spots are observed on the upper surface at the juvenile stage.

The mature of foliage displays upon its upper surface a near Moderate Olive Green, 5GY 4/3. The under surface is between Moderate Yellow Green, 5GY 5/6 and Moderate Yellow Green, 7.5GY 5/7.

The young foliage on its upper surface is also near Moderate Olive Green, 2.5 GY 4/3, the under surface being near Moderate Yellow Green, 5GY 5/6.

The rachis is light, being on its upper side grooved with some very small stipitate glands on the edges. The underside is smooth, except for occasional to few small prickles and very small stipitate glands.

The stipules are short, narrow, and with short points turning out at an angle of more than 45°.

The plant displays a more than average resistance to mildew, when compared with other varieties now in commerce and grown under comparable conditions at Ontario, Calif.

*Growth*

The plant is of bushy habit, being spreading and much branched. It is vigorous in growth, with light to medium caliper canes.

The main stems are near Moderate Yellow Green, 5GY 5/6, in color. They bear several to many medium-length large prickles, hooked slightly downward, and with moderately short-narrow base. The color of these large prickles is near Strong Yellowish Brown, 7.5YR 5/7. There are also several to many small prickles, corresponding in color to the large prickles. There are no hairs.

The branches are near Moderate Yellow Green, 7.5GY 5/7, in color. They carry several to many large prickles, these being medium-length, hooked slightly downward, with moderately short, narrow base. Their color is near Strong Greenish Yellow, 7.5Y 7/9. There are several to many small prickles which are the same coloration as the large prickles. There are no hairs.

The new shoots are near Light Olive, 10Y 5/5, overlaid with near Moderate Yellowish Brown, 10YR 4/4, on the side exposed to the sun. There are several to many large prickles of medium length, hooked slightly downward, with moderately short, narrow base. There are few small prickles. Both the large prickles and the small prickles are near Moderate Reddish Brown, 10R 3/4, in color. There are no hairs.

I claim:

1. A new variety of rose plant of the floribunda class, substantially as herein illustrated and described, being characterized by a plurality of combinations of the following features, namely, the distinctive coloration of the bloom, particularly when grown in areas of low light intensity, under which conditions the flower petals are consistently rimmed with paler color, especially in early summer and autumn, the rimmed effect being less conspicuous in hot sun and in mid-summer; the petals numbering from fifteen to twenty-five approximately, and including five to eight petaloids, said blooms being between about 2½" and 3⅓" in diameter, usually one to a stem, although occasionally growing several to a stem in an irregular cluster; the plant itself being bushy, spreading and thickly branched in its habit of growth, and transiently displaying, on newly developed foliage, small raised dark green areas, said plant further being characterized in that the length and caliper of the stipitate glands carried on the peduncles is substantially smaller than in normal plants of this genus.

No references cited.

ROBERT E. BAGWILL, Primary Examiner

UNITED STATES PATENT OFFICE
CERTIFICATE OF CORRECTION

Patent No. PP 3351 Dated June 5, 1973

Inventor(s) Samuel McGredy, IV

It is certified that error appears in the above-identified patent and that said Letters Patent are hereby corrected as shown below:

Column 2, line 65 - "1/3" should be --1/2--

Column 3, line 38 - "10R 4/12" should be --10RP4/12--

Column 4, line 33 - the hyphen (-) should be a comma (,)

Column 4, line 63 - "1/3" should be --1/2--

Signed and sealed this 16th day of July 1974.

(SEAL)
Attest:

McCOY M. GIBSON, JR.
Attesting Officer

C. MARSHALL DANN
Commissioner of Patents

USCOMM-DC 60376-P69
* U.S. GOVERNMENT PRINTING OFFICE : 1969 O—366-334